US007841336B2

(12) United States Patent
Rivera et al.

(10) Patent No.: US 7,841,336 B2
(45) Date of Patent: Nov. 30, 2010

(54) NEBULIZE WITH PRESSURE-BASED FLUIDIC CONTROL AND RELATED METHODS

(75) Inventors: David A. Rivera, Yorba Linda, CA (US); Steven M. Harrington, Cardiff by the Sea, CA (US); Bruce K. Bridges, Cardiff, CA (US); Neil A. Korneff, Diamond Bar, CA (US)

(73) Assignee: CareFusion 2200, Inc., San Diego, CA (US)

( * ) Notice: Subject to any disclaimer, the term of this patent is extended or adjusted under 35 U.S.C. 154(b) by 845 days.

(21) Appl. No.: 11/729,720

(22) Filed: Mar. 29, 2007

(65) Prior Publication Data

US 2007/0227536 A1 Oct. 4, 2007

Related U.S. Application Data

(60) Provisional application No. 60/787,195, filed on Mar. 30, 2006, provisional application No. 60/787,196, filed on Mar. 30, 2006.

(51) Int. Cl.
*A61M 11/00* (2006.01)

(52) U.S. Cl. ............................ 128/200.21; 128/200.18; 128/200.14

(58) Field of Classification Search ................................ 128/200.18–200.21, 202.28, 202.25, 203.11, 128/203.12, 203.15; 239/338
See application file for complete search history.

(56) References Cited

U.S. PATENT DOCUMENTS

| | | | | |
|---|---|---|---|---|
| 4,116,387 | A | 9/1978 | Kremer, Jr. et al. | |
| 4,278,110 | A | 7/1981 | Price et al. | |
| 4,560,519 | A * | 12/1985 | Cerny | 261/78.2 |
| 5,080,093 | A * | 1/1992 | Raabe et al. | 128/203.12 |
| 6,595,203 | B1 * | 7/2003 | Bird | 128/200.21 |
| 6,644,304 | B2 * | 11/2003 | Grychowski et al. | 128/200.18 |
| 6,679,250 | B2 * | 1/2004 | Walker et al. | 128/200.21 |

FOREIGN PATENT DOCUMENTS

| | | | |
|---|---|---|---|
| EP | 0281650 | A1 | 9/1988 |
| EP | 0855224 | A2 | 7/1998 |
| EP | 0938906 | A2 | 9/1999 |
| FR | 2751883 | A1 | 2/1998 |
| WO | 03/053500 | A1 | 7/2003 |

OTHER PUBLICATIONS

PCT International Preliminary Report and Written Opinion mailed Oct. 9, 2008 (14 pages).

* cited by examiner

*Primary Examiner*—Steven O Douglas
(74) *Attorney, Agent, or Firm*—Dicke, Billig & Czaja, PLLC

(57) ABSTRACT

Various embodiments of a breath-activated nebulizer with fluidic control and related methods of using such a nebulizer are disclosed. The nebulizer may include a body comprising a reservoir for holding medication, a nozzle for emitting a jet of pressurized gas, and a fluid conduit in communication with the reservoir for delivery of the medication proximate the jet to produce an aerosol of medication. The nebulizer may also include a nebulizer outlet in communication with an interior of the body for delivery of the aerosol to a patient, a control conduit in fluid communication with the fluid conduit for delivery of a control gas to the fluid conduit to prevent the delivery of the medication proximate the jet, and a fluidic amplifier configured to control the delivery of the control gas to the control conduit.

78 Claims, 8 Drawing Sheets

NEBULIZE WITH PRESSURE-BASED FLUIDIC CONTROL AND RELATED METHODS

This application claims the benefit of priority under 35 U.S.C. §119(e) of U.S. Provisional Application Nos. 60/787,195 and 60/787,196, both filed Mar. 30, 2006. This application also relates to commonly assigned U.S. application Ser. No. 11/729,608 of Steven M. Harrington et al., entitled "NEBULIZER WITH FLOW-BASED FLUIDIC CONTROL AND RELATED METHODS" and filed on the same date as the present application. The complete subject matter of each of the above-referenced applications is incorporated by reference herein.

FIELD OF THE INVENTION

Embodiments of the present invention relate generally to medical devices and related methods. More specifically, particular embodiments of the invention relate to a nebulizer system with fluidic control and related methods of using such a system.

DESCRIPTION OF RELATED ART

Nebulizers, also known as atomizers, are typically used to treat certain conditions or diseases that require medication to be delivered directly to the respiratory tract. To deliver medication to the respiratory tract, conventional nebulizers may use pressurized gas to nebulize liquid medication into aerosol that can be inhaled by a patient. In general, a reservoir containing the liquid medication or an orifice in communication with the reservoir is positioned adjacent an outlet of the pressurized gas, and when the pressurized gas passes over the reservoir or the orifice, a negative pressure is created in the vicinity of the outlet, causing the liquid medication to be drawn out of the reservoir and entrained into the stream of pressurized gas. The stream of pressurized gas with entrained liquid medication forms aerosol particles that are suspended within the nebulizer for inhalation by a patient.

In various conventional nebulizers, aerosol is continuously generated until the liquid medication in the reservoir is depleted. Such continuous nebulization causes a significant portion of the medication to be wasted into the environment when the patient is not inhaling. Also, it may be difficult to quantify the precise amount of aerosol that has been administered to the patient. To reduce such a waste, nebulizers with bag reservoir systems that collect generated aerosol between inhalations have been suggested. These systems, however, are bulky and difficult to set up. Moreover, studies have shown that a portion of the collected aerosol is deposited or condensed on the inner walls of the reservoir systems without ever being delivered to the patient.

Some nebulizers generate aerosol in a non-continuous manner, such as, for example, in response to a patient's breath. Such devices are more efficient than the above-mentioned, continuous nebulizers because the medication is not wasted when the patient is not inhaling. Certain nebulizers of this type utilize a movable diverter, positioned relative to the pressurized gas outlet or nozzle, to selectively nebulize the liquid medication. For example, the diverter may be movable between a non-nebulizing position and a nebulizing position in response to a patient's breath. When the patient is not inhaling, the diverter is in the non-nebulizing position (e.g., with a sufficient distance from the outlet of the pressurized gas) and no nebulization occurs in the nebulizer. Upon patient inhalation, a negative pressure is created inside the nebulizer, which causes the diverter to move to a nebulizing position (e.g., closer to the outlet of the pressurized gas) to divert the pressurized gas over the reservoir or the orifice of the reservoir. The high velocity air diverted over the reservoir or the orifice of the reservoir causes the liquid medication to be entrained and nebulized. At the end of the patient inhalation, the diverter is moved back to the non-nebulizing position by, for example, a spring, and the nebulization stops.

Nebulizers employing movable parts for actuation, however, have certain drawbacks. For example, while nebulizers are often intended for multiple uses, the aerosolized medication may dry out inside the nebulizer after use and may cause the movable parts to stick to non-moving parts, rendering the nebulizer inoperative for reuse. To eliminate the possibility of this sticking problem, the nebulizers may require thorough cleaning and/or disassembly of the nebulizer parts after each use. Moreover, the movable actuation system requires costly diaphragms and/or springs to cause movement of the moving parts. In addition, due to the relatively small tolerances required in such nebulizers (e.g., close control of the distance between the diverter and the gas outlet), design and manufacturing of movable actuation systems may pose difficulties.

Accordingly, there is a need for an improved nebulizer that may overcome one or more of the problems discussed above. In particular, there is a need for an improved actuation system with a minimum number of moving parts, while maintaining optimal performance.

SUMMARY OF THE INVENTION

Therefore, various exemplary embodiments of the invention may provide an improved nebulizer system with a stationary diverter and a fluidic control system to selectively actuate the nebulization process. There are several advantages of a nebulizer system with a fluidic control system. For example, in addition to its capabilities to overcome one or more problems discussed above, a fluidic control system, being extremely sensitive to pressure changes, may provide the potential of enabling control of the nebulization process at lower inspiratory flows than the conventional technology. This may result in faster and/or more consistent delivery of medication to the patient. Moreover, such fluidic control systems may allow a nebulizer system to be used on patients that may have the ability to produce only lower inspiratory pressure, such as children or the elderly.

In addition, the control mechanism of the present invention may not require a significant level of negative pressure to initiate nebulization. Thus, a substantially less vacuum is needed to initiate nebulization, and a patient may experience less resistance during inhalation. Moreover, a lower threshold level of negative pressure may reduce the need to create a tighter seal at the patient interface (e.g., mouthpiece or face masks), thereby improving patient comfort.

While the present invention will be described in connection with a nebulizer system for nebulizing medication, embodiments of the invention may be used in other suitable medical and non-medical applications, such as, for example, veterinarian applications and on-demand humidification systems. Also, while the present invention will be described in connection with a breath-actuated nebulizer system, certain embodiments of the invention may include an interface device, such as a mechanical ventilator, for patients that are unable to breath enough on their own to trigger nebulization. In such cases, the interface device may be used to trigger the nebulizer system to nebulize liquid medication for delivery to the patient.

To attain the advantages and in accordance with the purpose of the invention, as embodied and broadly described herein, one exemplary aspect of the invention may provide a nebulizer including a body comprising a reservoir for holding medication, a nozzle for emitting a jet of pressurized gas, and a fluid conduit in communication with the reservoir for delivery of the medication proximate the jet to produce an aerosol of medication. The nebulizer may also include a nebulizer outlet in communication with an interior of the body for delivery of the aerosol to a patient, a control conduit in fluid communication with the fluid conduit for delivery of a control gas to the fluid conduit to prevent the delivery of the medication proximate the jet, and a fluidic amplifier configured to control the delivery of the control gas to the control conduit. In some exemplary aspects, the fluidic amplifier is configured to control the delivery of the control gas to the control conduit based on inhalation by the patient.

According to another exemplary aspect, the nebulizer may further comprise a signal conduit in fluid communication with the fluidic amplifier. The signal conduit may provide a negative pressure in response to the inhalation by the patient, and the negative pressure may cause interruption of the delivery of the control gas to the fluid conduit via the control conduit.

In various exemplary aspects, the fluidic amplifier may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient. The control port may be in fluid communication with the nebulizer outlet.

In another exemplary aspect, the fluidic amplifier may be configured such that the inhalation by the patient causes a negative pressure in the control port, causing a flow direction of the control gas to switch from the second outlet port to the first outlet port.

In still another exemplary aspect, the first outlet port may be in fluid communication with atmosphere.

According to one exemplary aspect, the fluidic amplifier may further comprise an input flow port disposed substantially opposite to the control port with respect to the inlet port. The first outlet port may be in fluid communication with the input flow port.

According to another exemplary aspect, the control port may comprise a valve configured to close in response to the inhalation by the patient.

In some exemplary aspects, the pressurized gas and the control gas may be delivered from a same source of gas. For example, the control gas may be branched off from the pressurized gas.

According to another exemplary aspect, the nebulizer may further comprise a flow regulator for controlling a flow of the control gas. For example, the flow regulator may comprise a through-hole in a sleeve that at least partially defines the fluid conduit. In still another exemplary aspect, the nebulizer may comprise a stationary diverter to which the jet of pressurized gas is directed. In yet still another exemplary aspect, the nebulizer outlet may comprise a venturi through which fluid passes when the patient inhales through the nebulizer outlet. The venturi may be located inside the nebulizer outlet and is in fluid communication with the fluidic amplifier. Alternatively, the venturi is located inside the body and is in fluid communication with the fluidic amplifier.

In another exemplary aspect, the nebulizer may comprise an override mechanism configured to selectively disable operation of the fluid amplifier.

Some exemplary aspects of the invention may provide a nebulizer comprising a body comprising a reservoir for holding medication, a nozzle for emitting a jet of pressurized gas, a fluid conduit in communication with the reservoir for delivery of the medication proximate the jet to produce an aerosol of medication, and a nebulizer outlet in communication with an interior of the body for delivery of the aerosol to a patient. The nebulizer may also comprise a control conduit in fluid communication with the fluid conduit for delivery of a control gas to the fluid conduit to prevent the delivery of the medication proximate the jet, and a flow switch configured to control the delivery of the control gas to the control conduit based on inhalation by the patient. The flow switch may include no part that moves in response to the inhalation by the patient.

In an exemplary aspect, the nebulizer may comprise a signal conduit in fluid communication with the flow switch, the signal conduit for providing a negative pressure in response to the inhalation by the patient, the negative pressure for causing interruption of the delivery of the control gas to the fluid conduit via the control conduit.

In another exemplary aspect, the flow switch may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient. The control port may be in fluid communication with the nebulizer outlet.

In one exemplary aspect, the flow switch may be configured such that the inhalation by the patient causes a negative pressure in the control port, causing a flow direction of the control gas to switch from the second outlet port to the first outlet port. In another exemplary aspect, the first outlet port may be in fluid communication with atmosphere or an interior of the body.

In still another exemplary aspect, the flow switch may further comprise an input flow port disposed substantially opposite to the control port with respect to the inlet port. The first outlet port may be in fluid communication with the input flow port.

According to another exemplary aspect, the pressurized gas and the control gas may be delivered from a same source of gas. For example, the control gas may be branched off from the pressurized gas. Still another exemplary aspect may provide a flow regulator for controlling a flow of the control gas. The flow regulator may comprise a through-hole in a sleeve that at least partially defines the fluid conduit.

In one exemplary aspect, the nebulizer may further comprise a venturi through which fluid passes when the patient inhales through the nebulizer outlet. The venturi may be located inside the nebulizer outlet and may be in fluid communication with the flow switch. Alternatively, the venturi may be located inside the body and may be in fluid communication with the flow switch.

In still another exemplary aspect, the nebulizer may further comprise an override mechanism configured to selectively disable operation of the flow switch.

According to various exemplary aspects, a nebulizer may comprise a body comprising a reservoir for holding medication, a nozzle for emitting a jet of pressurized gas, a fluid conduit in communication with the reservoir for delivery of the medication proximate the jet to produce an aerosol of medication, and a nebulizer outlet in communication with an interior of the body for delivery of the aerosol to a patient. The nebulizer may also comprise a control conduit in fluid communication with the fluid conduit for delivery of a control gas to the fluid conduit to prevent the delivery of the medication proximate the jet, and a flow switch. The flow switch may comprise an inlet port for receiving the control gas, a first outlet port, a second outlet port for directing the control gas to the fluid conduit, and a control member configured to selectively switch a flow direction of the control gas between the first outlet port and the second outlet port. In another exemplary aspect, the control member may be configured to switch the flow direction based on inhalation by the patient.

In one exemplary aspect, the control member may comprise a control port in fluid communication with the nebulizer outlet via a signal conduit. The signal conduit may provide a negative pressure in response to the inhalation by the patient for causing a flow direction of the control gas to switch from the second outlet port to the first outlet port, so as to interrupt the delivery of the control gas to the control conduit.

In another exemplary aspect, the control member may comprise a valve configured to selectively open the first outlet port in response to the inhalation by the patient, opening the first outlet port causing the flow direction of the control gas to switch from the second outlet port to the first outlet port.

In still another exemplary aspect, the flow switch may comprise a T-junction with each branch constituting the inlet port, the first outlet port, and the second outlet port, respectively.

In yet still another exemplary aspect, the first outlet port may be in fluid communication with atmosphere. In one exemplary aspect, the flow switch may include no part that moves in response to the inhalation by the patient.

According to some exemplary aspect, the pressurized gas and the control gas may be delivered from a same source of gas, with the control gas being branched off from the pressurized gas. According to another exemplary aspect, the nebulizer may comprise a flow regulator for controlling a flow of the control gas. In still another exemplary aspect, the flow regulator may comprise a through-hole in a fluid sleeve that at least partially defines the fluid conduit.

In one exemplary aspect, the nebulizer may comprise a venturi through which fluid passes when the patient inhales through the nebulizer outlet. In still another exemplary aspect, the nebulizer may further comprise an override mechanism configured to selectively disable operation of the flow switch.

One exemplary aspect may provide a nebulizer comprising a body comprising a reservoir for holding medication, a nozzle for emitting a jet of pressurized gas with the pressurized gas supplied to the nozzle via a main gas conduit, and a fluid conduit in communication with the reservoir for delivery of the medication proximate the jet to produce an aerosol of medication. The nebulizer may also comprise a nebulizer outlet in communication with an interior of the body for delivery of the aerosol to a patient, a control conduit branching off from the main gas conduit and in fluid communication with the fluid conduit, the control conduit for delivery of a control gas to the fluid conduit to prevent the delivery of the medication proximate the jet, and a control system configured to control the delivery of control gas to the control conduit. In some exemplary aspects, the control system may be configured to control the delivery of control gas to the control conduit based on inhalation by the patient.

According to another exemplary aspect, the nebulizer may comprise a signal conduit in fluid communication with the control system, where the signal conduit may provide a negative pressure in response to the inhalation by the patient. The negative pressure may cause interruption of the delivery of the control gas to the fluid conduit via the control conduit.

In some exemplary aspects, the control system may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient. The control port may be in fluid communication with the nebulizer outlet.

According to another exemplary aspect, the nebulizer may comprise a flow regulator for controlling a flow of the control gas to the control conduit. In still another exemplary aspect, the nebulizer may comprise a stationary diverter to which the jet of pressurized gas is directed. In yet still another exemplary aspect, the control system may include no part that moves in response to the inhalation by the patient.

Various exemplary aspects of the invention may provide a method of controlling a nebulization process. The method may comprise providing medication in a reservoir within a body, where the body comprising an outlet for inhalation by a patient, emitting a jet of pressurized gas into the body, and providing a fluid conduit in communication with the reservoir for delivery of the medication proximate the jet. The method may also comprise preventing delivery of the medication proximate the jet by delivering a control gas to the fluid conduit via a control conduit, and using a fluidic amplifier to interrupt the delivery of the control gas to the control conduit based on inhalation by the patient. The interruption may permit delivery of the medication proximate the jet to produce an aerosol of medication.

In another exemplary aspect, the fluidic amplifier may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient.

In some exemplary aspects, the control port may be in fluid communication with the outlet. The method may further comprise creating a negative pressure in the control port by inhalation of the patient. The negative pressure may cause a flow direction of the control gas to switch from the second outlet port to the first outlet port. According to another exemplary aspect, the first outlet port may communicate with atmosphere.

According to still another exemplary aspect, the method may further comprise biasing the control gas to flow from the inlet port to the second outlet port when the patient is not inhaling.

In one exemplary aspect, the pressurized gas and the control gas may be delivered from a same source of gas. For example, the control gas may be branched off from the pressurized gas.

In another exemplary aspect, the method may further comprise regulating a flow of the control gas to the control conduit via a flow regulator. In still another exemplary aspect, the method may comprise directing the jet of pressurized gas towards a stationary diverter. In yet still another exemplary aspect, the fluidic amplifier may include no part that moves in response to the inhalation by the patient.

According to an exemplary aspect, a method of controlling a nebulization process may comprise providing medication in a reservoir within a body, where the body comprises an outlet for inhalation by a patient, emitting a jet of pressurized gas, and providing a fluid conduit in communication with the reservoir for delivery of the medication proximate the jet. The method may also include preventing delivery of the medication proximate the jet by delivering a control gas to the fluid conduit, and using a flow switch to interrupt the delivery of the control gas to the control conduit based on inhalation by the patient, the interruption permitting delivery of the medication proximate the jet to produce an aerosol of medication. In various exemplary aspects, the flow switch may include no part that moves in response to the inhalation by the patient.

In an exemplary aspect, the flow switch may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient.

In another exemplary aspect, the control port may be in fluid communication with the outlet. The method may further comprise creating a negative pressure in the control port by inhalation of the patient. The negative pressure may cause a flow direction of the control gas to switch from the second outlet port to the first outlet port.

In still another exemplary aspect, the method may further comprise biasing the control gas to flow from the inlet port to the second outlet port when the patient is not inhaling.

According to another exemplary aspect, the pressurized gas and the control gas may be delivered from a same source of gas. For example, the control gas may be branched off from the pressurized gas.

Some exemplary aspects of the invention may provide a method of selectively controlling a nebulization process, comprising providing medication in a reservoir within a body, where the body comprises an outlet for inhalation by a patient, emitting a jet of pressurized gas, and providing a fluid conduit in communication with the reservoir for delivery of the medication proximate the jet. The method may further comprise preventing delivery of the medication proximate the jet by delivering a control gas to the fluid conduit via a control conduit, and using a flow switch to interrupt the delivery of the control gas to the control conduit. The flow switch may comprise an inlet port for receiving the control gas, a first outlet port, a second outlet port for directing the control gas to the fluid conduit, and a control member configured to switch a flow direction of the control gas between the first outlet port and the second outlet port. In another exemplary aspect, the control member may be configured to switch the flow direction of the control gas between the first outlet port and the second outlet port based on inhalation by the patient.

In one exemplary aspect, the control member may comprise a control port in fluid communication with the outlet via a signal conduit. The signal conduit may provide a negative pressure in response to the inhalation by the patient for causing a flow direction of the control gas to switch from the second outlet port to the first outlet port, so as to interrupt the delivery of the control gas to the control conduit.

In another exemplary aspect, the control member may comprise a valve configured to selectively open the first outlet port in response to the inhalation by the patient. Opening the first outlet port may cause the flow direction of the control gas to switch from the second outlet port to the first outlet port.

According to still another exemplary aspect, the flow switch may comprise a T-junction with each branch constituting the inlet port, the first outlet port, and the second outlet port, respectively. According to yet still another exemplary aspect, the pressurized gas and the control gas may be delivered from a same source of gas. For example, the control gas may be branched off from the pressurized gas.

In another exemplary aspect, a method of selectively controlling a nebulization process may comprise providing medication in a reservoir within a body, the body comprising an outlet for inhalation by a patient, emitting a jet of pressurized gas, the pressurized gas supplied via a main gas conduit, and providing a fluid conduit in communication with the reservoir for delivery of the medication proximate the jet. The method may further comprise preventing delivery of the medication proximate the jet by delivering a control gas to the fluid conduit via a control conduit, and using a control system to interrupt the delivery of the control gas to the control conduit based on inhalation by the patient. According one exemplary aspect, the control conduit may branch off from the main gas conduit and is in fluid communication with the fluid conduit.

In some exemplary aspects, the control system may comprise an inlet port for receiving the control gas, a first outlet port, a second outlet port for directing the control gas to the fluid conduit, and a control port configured to selectively switch a flow direction of the control gas between the first outlet port and the second outlet port based on the inhalation by the patient.

According to another exemplary aspect, the method may further comprise connecting the control port to the outlet, so that the inhalation by the patient creates a negative pressure for causing the flow direction of the control gas to switch from the second outlet port to the first outlet port, so as to interrupt the delivery of the control gas to the control conduit.

In still another exemplary aspect, the control system may include no part that moves in response to the inhalation by the patient.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

DESCRIPTION OF THE EMBODIMENTS

Reference will now be made in detail to exemplary embodiments consistent with the present invention, examples of which are illustrated in the accompanying drawings. Wherever possible, the same reference numbers will be used throughout the drawings to refer to the same or like parts.

Figure 1:
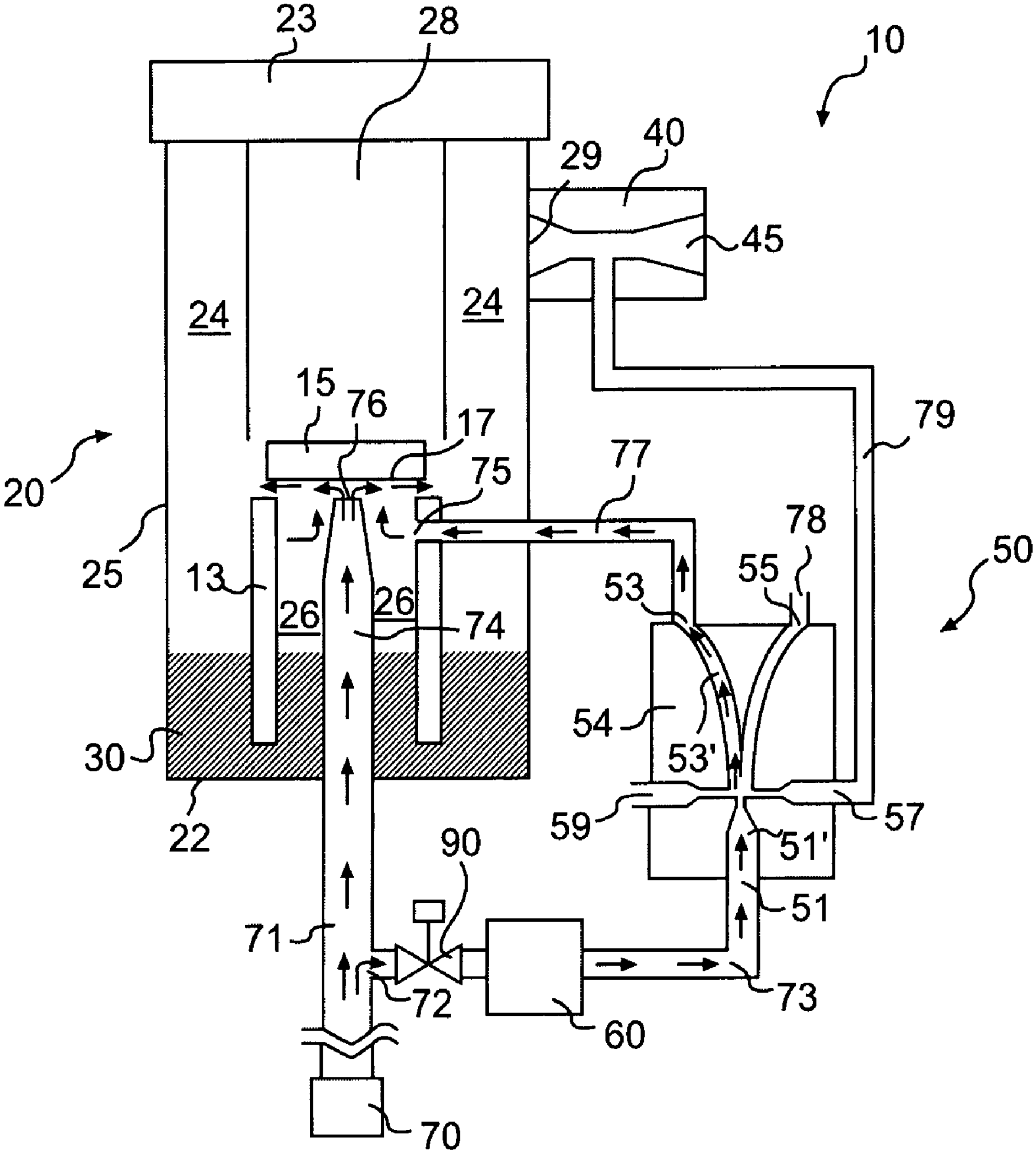
FIG. 1 is a schematic view of a nebulizer system, according to an exemplary embodiment of the invention, illustrating a non-nebulizing mode.
Figure 2:
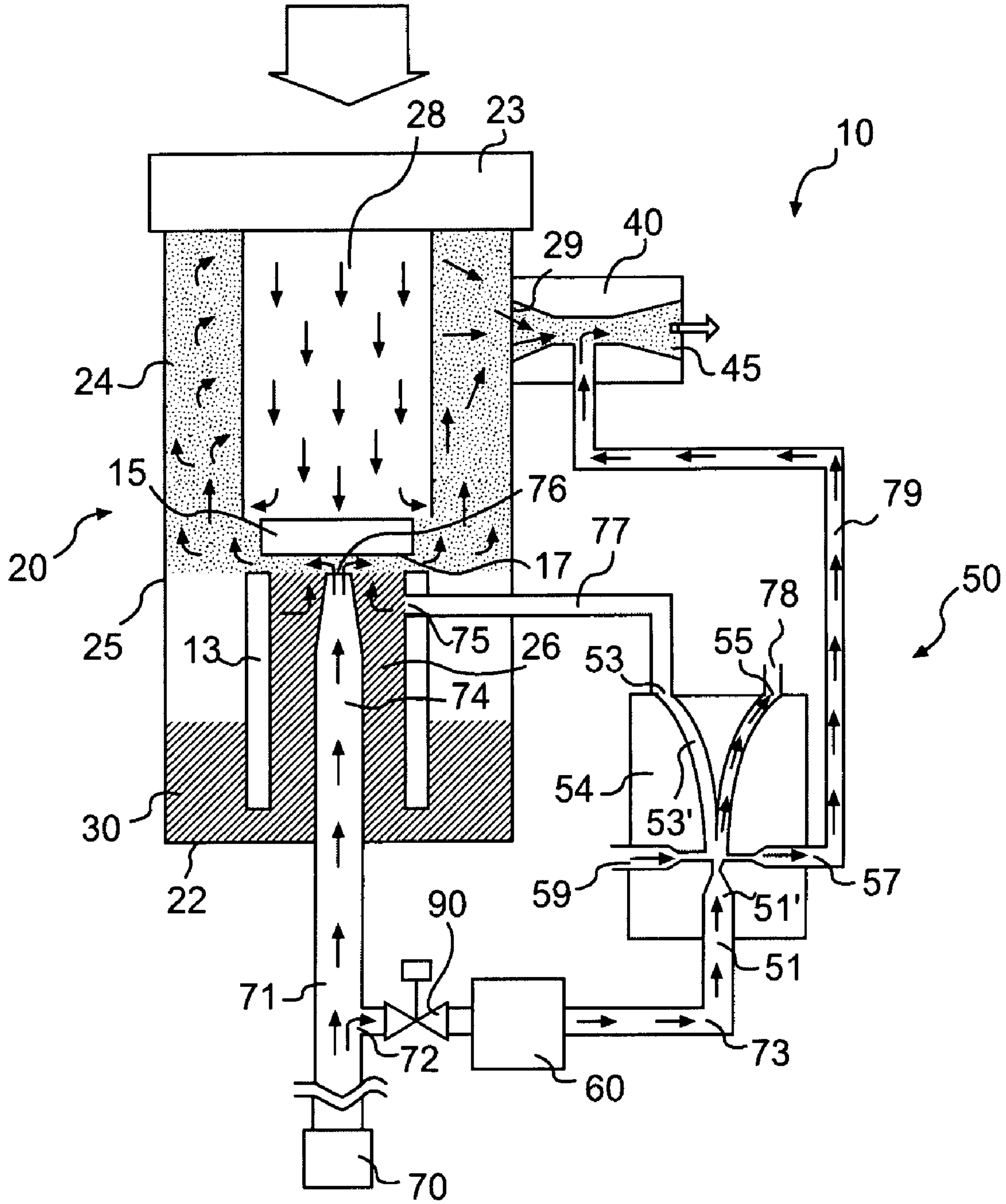
FIG. 2 is a schematic view of the nebulizer system of FIG. 1, illustrating a nebulizing mode.

FIGS. 1 and 2 show a breath-actuated nebulizer system 10 with a pressure-based fluid control mechanism, according to an exemplary embodiment of the invention. The system 10 may comprise a nebulizer body 20 defining an interior space 24 and an outlet port 29 in fluid communication with the interior space 24 for delivery of the nebulized medication to a patient. The system 10 may also comprise a pressurized gas source 70 (e.g., at approximately 50 psi) for use in a nebulization process and a fluidic control system 50 for selectively actuating the nebulization process in response to patient's inhalation.

Figure 1A:
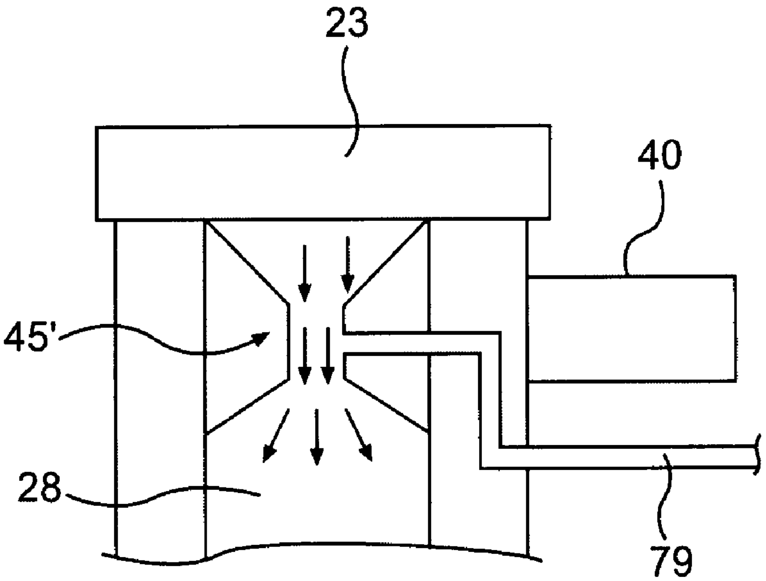
FIG. 1A is a partial schematic view of a nebulizer system, according to another exemplary embodiment of the invention, illustrating that a venturi may be placed near an air entrainment port.

The nebulizer body 20 may comprise a generally cylindrical body 25 defining the interior space 24 and a fluid reservoir 22 for containing medication 30 (e.g., in the form of liquid) intended for nebulization. The fluid reservoir 22 may have a variety of different shapes and sizes. For example, in some exemplary embodiments, the reservoir 22 may have a conical shape. An outlet member 40 (e.g., a mouthpiece) may extend from the nebulizer body 20 and communicate with the outlet port 29. In an exemplary embodiment, a venturi 45 may be formed by or positioned inside of the outlet member 40 to amplify the negative pressure caused by the patient inhalation. The venturi 45 may be placed at any location along the air passage between an air entrainment port 28 and the outlet port 29. For example, in some exemplary embodiments, as shown in FIG. 1A, the venturi 45' may be placed near the air entrainment port 28. The functional aspect of the venturi 45, 45' will be described further herein.

At an upper portion of the nebulizer body 20, the air entrainment port 28 may include a pressure regulator 23 to control air entrainment flow into the interior space 24 during the patient inhalation. A certain threshold level of vacuum inside the interior space 24 may aid the actuation of the fluidic control system 50, and the pressure regulator 23 at the air entrainment port 28 may be used to maintain the interior space 24 at an optimal vacuum level during the patient inhalation. For example, when the patient inhales, a vacuum is created in the interior space 24. After a predetermined threshold vacuum is reached, the normally-closed pressure regulator 23 may open to allow outside air to entrain into the interior space 24. Opening the pressure regulator 23 may eliminate any excessive resistance to the patient inhalation caused by excessive vacuum in the interior space 24, while maintaining the vacuum above the threshold level. In some exemplary embodiments, the pressure regulator 23 may include one or more openings, the size of which may vary depending upon the flow rate of the entrained air. In another exemplary embodiment, the pressure regulator 23 may include a spring-loaded member, or other biased member such as a flexible valve or diaphragm, and may automatically fully close at the end of the patient inhalation.

As shown in FIGS. 1 and 2, pressurized gas (e.g., air) from the pressurized gas source 70 may be directed towards a diverter 15 (e.g., a baffle) to cause nebulization of the medication 30. The diverter 15 is preferably stationary. In various exemplary embodiments, the pressurized gas may be accelerated through a nozzle 74 to an outlet 76 to create an aerosol jet impinging on the diverter 15. The nozzle 74 may extend from the bottom of the nebulizer body 20 in a direction substantially parallel to a longitudinal axis of the nebulizer body 20. The outlet 76 of the nozzle 74 may face the diverter 15 in a direction substantially perpendicular to an impingement surface 17 of the diverter 15. Adjacent the diverter 15 and around the nozzle 74, a fluid sleeve 13 (e.g., annular sleeve) defining a conduit 26 (e.g., annular conduit) may be provided for transporting the medication 30 from the fluid reservoir 22 to the aerosol jet during nebulization. The distance between the outlet 76 of the nozzle 74 and the impingement surface 17 of the diverter 15 may be sufficiently close, such that, during nebulization, the pressurized gas diverted by the diverter 15 may create a sufficient negative pressure in the conduit 26 to cause the medication 30 to be transported to the conduit 26 and entrained into the aerosol jet for nebulization.

As mentioned above, the fluidic control system 50 may be used to selectively actuate the nebulization process in the nebulizer body 20 in response to the patient inhalation. The control system 50 may use a fluidic amplifier 54 and a control flow branched out of the pressurized gas source 70 to switch between the nebulizing and non-nebulizing modes. The operation of the fluidic amplifier 54 will be described later with reference to FIGS. 3-12. To direct the control flow from the pressurized gas source 70, a control flow manifold 72 (e.g., a T-junction) may be positioned in the main pressurized gas line 71 to create a pressure drop therein and thereby create a low-flow (e.g., approximately 2-5 lpm), low-pressure (e.g., approximately 50-70 cm water) flow to the fluidic amplifier 54. The manifold 72 may use an orifice and/or varied geometries of the flow path to achieve the desired pressure drop.

The system 10 may also include a control flow regulator 60 located, for example, between the control flow manifold 72 and the fluidic amplifier 54. In some exemplary embodiments, the flow regulator 60 may be placed at any location between the fluid amplifier 54 and the fluid conduit 26. The regulator 60 may be configured to maintain the control flow to the conduit 26 within a certain flow rate range. For example, when the flow rate of the control flow exceeds a specified threshold value, the control flow regulator 60 may vent excess flow out to atmosphere to maintain the control flow within the desired range. In an exemplary embodiment, the control flow regulator 60 may include a weighted float disposed over a fixed orifice and, when the control flow rate exceeds a specified threshold valve, the weighted float may be lifted to release the excess pressure to atmosphere. In some embodiments, the float may be held in place with a spring to lift the float. Any other suitable flow regulation techniques known in the art may also be used alternatively or additionally.

Maintaining the flow rate of the control flow within a certain range may be important for various reasons. For example, if the flow rate is too high, a greater pressure signal (e.g., a negative pressure created by patient inhalation) may be required to actuate the fluidic amplifier 54 to switch from the non-nebulizing mode to the nebulizing mode. In addition, the high flow rate may cause the control flow to flow down into the fluid reservoir 22, thereby causing undesirable bubbling in the reservoir 22. Moreover, it may be desirable to regulate gas entering the fluidic amplifier 54 to account for various pressurizing gas systems with varying source pressures.

Figure 1B:
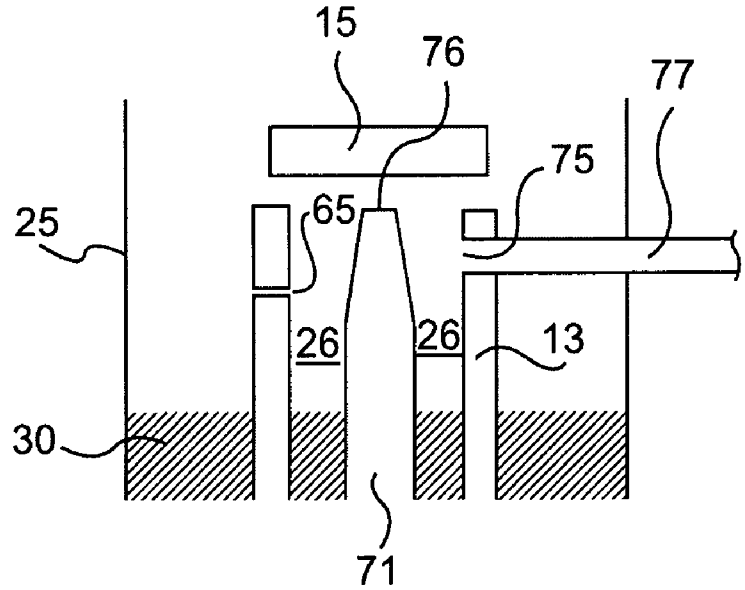
FIG. 1B is a partial schematic view of a nebulizer system, according to still another exemplary embodiment of the invention, illustrating an alternative or additional control flow regulator.

In some exemplary embodiments, the system 10 may regulate the control flow after it reached the fluid conduit 26. For example, in place of, or in addition to, the flow regulator 60 discussed above, the system 10 may include a through-hole 65 in the fluid sleeve 13, as shown in FIG. 1B. The through-hole 65 may provide a flow passage for excessive control flow to vent out of the fluid conduit 26, thereby preventing the excessive control flow from reaching down the reservoir 22 and causing undesirable bubbling. The through-hole 65 may be positioned below the exit portion 75 of the nebulizer flow path 77 and at substantially opposite side facing the exit portion 75. The opening area of the through-hole 65 may be smaller than the opening area of the exit portion 75. By way of examples only, the through-hole 65 may have an opening area that is 0.4-0.6 times the opening area of the exit portion 75. The through-hole 65 may be sufficiently small such that, during nebulization, the liquid medication 30 may effectively seal or block the through-hole 65, preventing air from entering into the conduit 26 through the through-hole 65.

In various exemplary embodiments, the nebulizer system 10 may include a suitable override mechanism configured to override breath actuation function of the nebulizer system 10 to continuously generate aerosol. The override mechanism may be controlled manually or automatically. In various exemplary embodiments, the override mechanism may include a valve 90 configured to selectively open and close the control flow passage from the control flow manifold 72 to the conduit 26. Thus, the valve 90 may be disposed at any location between the control flow manifold 72 and the conduit 26. In one exemplary embodiment, as shown in FIGS. 1 and 2, the valve 90 may be placed near the control flow manifold 72 before the flow regulator 60. When the valve 90 is actuated, the valve 90 closes the control flow path to prevent the control flow from reaching the conduit 26, regardless of whether the patient is inhaling or not. Thus, the breath actuation function of the nebulizer system 10 may be disabled, and the nebulized medication may be continuously generated. When the valve 90 is not actuated, the valve 90 may be biased in an open position to enable the breath actuation function of the nebulizer system 10.

In some alternative embodiments, the override mechanism may include a relief valve (not shown) configured to vent the control flow into atmosphere. When the relief valve is actuated, the control flow flowing through the control flow path may be vented to atmosphere. As a result, the control flow may not reach the conduit 26, thereby overriding the breath actuation function of the nebulizer system 10. In one exemplary embodiment, the relief valve may also function as the control flow regulator 60 for maintaining the control flow within a certain flow rate range. For example, the relief valve may be configured such that, when the flow rate of the control flow exceeds a predetermined threshold valve, the relief valve may open the relief passage to vent excess flow out to atmosphere to maintain the control flow within the desired range.

Figure 3:
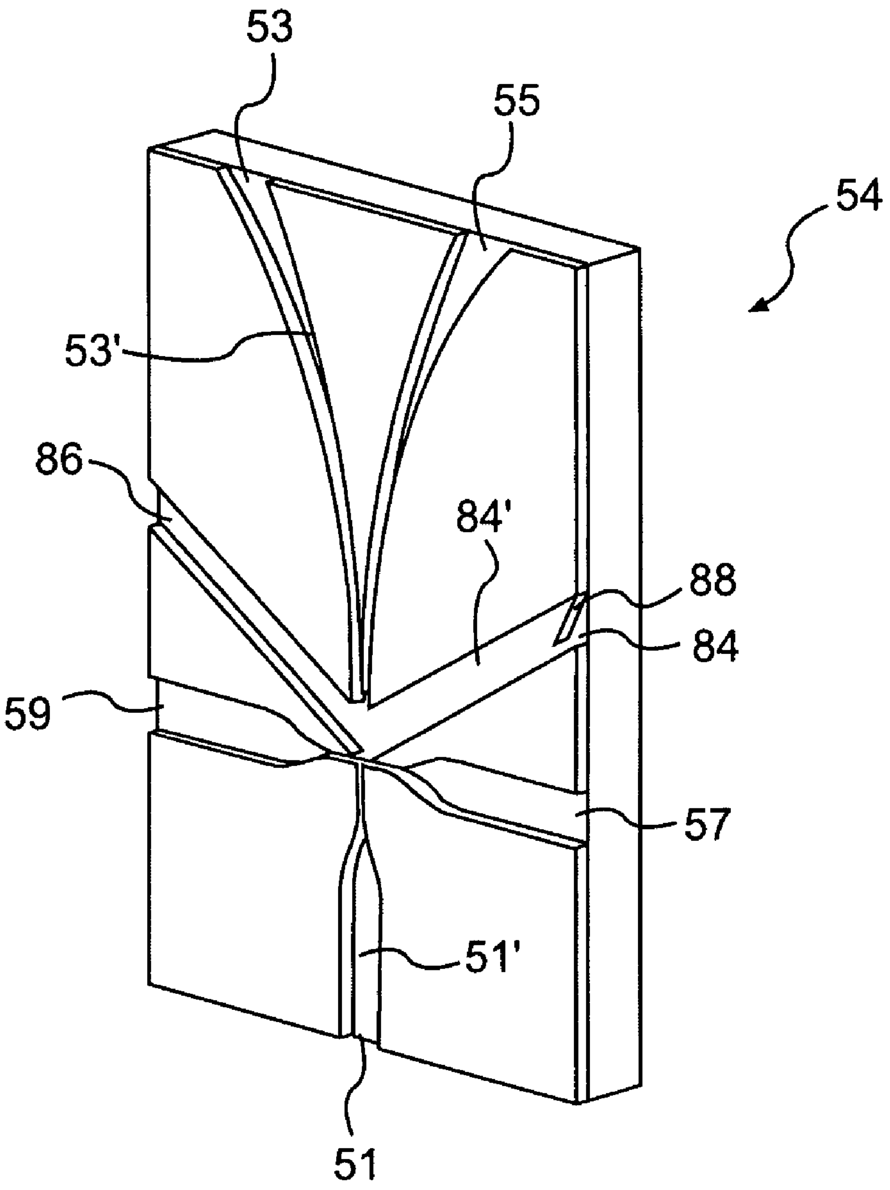
FIG. 3 is a cross-sectional, perspective view of a fluidic amplifier, according to an exemplary embodiment of the invention.

As best shown in FIG. 3, the fluidic amplifier 54 may comprise at least one inlet port 51, two outlet ports 53, 55, and one control port 57. As shown in FIGS. 1 and 2, the inlet port 51 may be in fluid communication with an inlet flow path 73 for receiving the control flow from the pressurized gas source 70. The control flow entering the inlet port 51 may be directed to one of the two outlet ports 53, 55 (i.e., a nebulizer port 53 and an ambient port 55). The nebulizer port 53 may be in fluid communication with a nebulizer flow path 77 for directing the control flow to an upper portion of the conduit 26 defined by the fluid sleeve 13. The fluid sleeve 13 may define an opening through which the exit portion 75 of the nebulizer flow path 77 may pass to communicate with the conduit 26. The ambient port 55 may be in fluid communication with a venting flow path 78 for directing the control flow to atmosphere. The control port 57 may be in fluid communication with a signal flow path 79 for receiving a switching signal from the venturi 45, 45' upon patient inhalation.

The fluidic amplifier 54 may also include an input flow port 59 configured to facilitate redirection of the control flow from the nebulizing port 53 to the ambient port 55. The input flow port 59 may be in fluid communication with atmosphere, or alternatively with the venting flow path 78. Upon patient inhalation, a negative pressure at the control port 57 may induce a flow of gas from the input flow port 59 to the control port 57 (with gas supplied from atmosphere or the venting flow path 78), as shown in FIG. 2. This flow of gas from the input flow port 59 to the control port 57 may facilitate redirection of the control flow from the nebulizing port 53 to the ambient port 55, thereby amplifying the switch signal generated by the patient inhalation to increase the sensitivity of the flow switch mechanism.

According to various exemplary embodiments, the fluidic amplifier 54 may be configured such that, when the patient is not inhaling, the control flow may enter the fluidic amplifier 54 via the inlet port 51 and exit the fluidic amplifier 54 via the nebulizer port 53, as shown in FIG. 1. In particular, an input channel 51' leading from the input port 51 may be aligned with a nebulizer channel 53' leading to the nebulizer port 53 so that the control flow, when under no influence of pressure, may be directed from the input channel 51' to the nebulizer channel 53'. In this non-nebulizing mode, the control flow exiting the fluidic amplifier 54 may enter into the conduit 26 inside the fluid sleeve 13 to disrupt the entrainment of the medication 30 into the aerosol jet.

When the patient inhales, as shown in FIG. 2, a negative pressure may be generated in the outlet member 40, which may be amplified by the venturi 45. The negative pressure may function as a triggering signal for the fluidic amplifier 54 to pull and redirect the control flow to the ambient port 55. This redirection may cause the control flow to be vented to atmosphere, thereby interrupting the control flow to the nebulizer port 53 and to the conduit 26. In this nebulizing mode, the medication 30 is allowed to transport up the conduit 26 inside the fluid sleeve 13 and entrain into the aerosol jet for nebulization. Once the patient inhalation stops and thereby the negative pressure diminishes and ceases, the control flow may switch back from the ambient port 55 to the nebulizer port 53, stopping the generation of nebulization, as shown in FIG. 1. In an exemplary embodiment, the fluidic amplifier 54 may be designed to switch between the non-nebulizing and nebulizing modes in less than 10 msec.

According to another exemplary embodiment of the invention, the fluidic amplifier 54 may also include a valved port 84 having a movable check valve 88 (e.g., a flexible diaphragm) and a corresponding input flow port 86 in fluid communication with atmosphere, as best shown in FIG. 3. The valved port 84 may be in fluid communication with the signal flow path 79, and the check valve 88 may be configured to respond to the negative pressure caused by the patient inhalation. For example, when the patient inhales, the check valve 88 may close off the valved port 84. Closing off the valved port 84 may cause a turbulence within the valve (for example, within channel 84'), which assists in redirection of the control flow from nebulizer port 53 to the ambient port 55.

Figure 4:
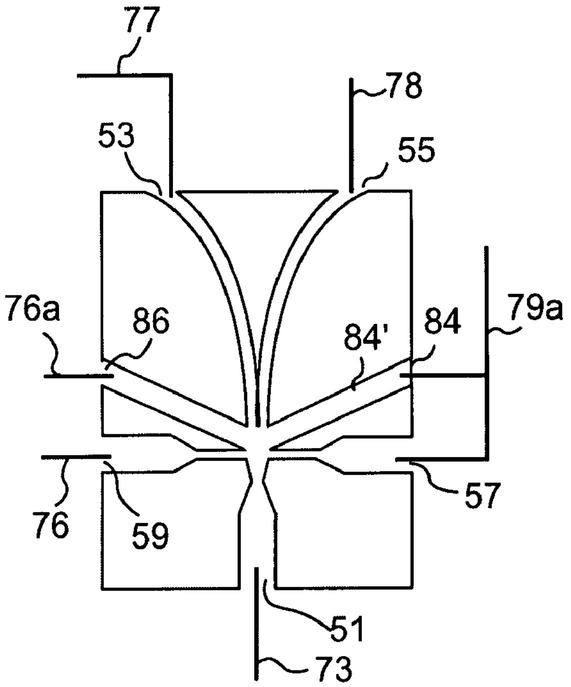
FIGS. 4-7 are schematic illustrations of flow connections in the fluidic amplifier shown in FIG. 3, according to various exemplary embodiments of the invention.
Figure 5:
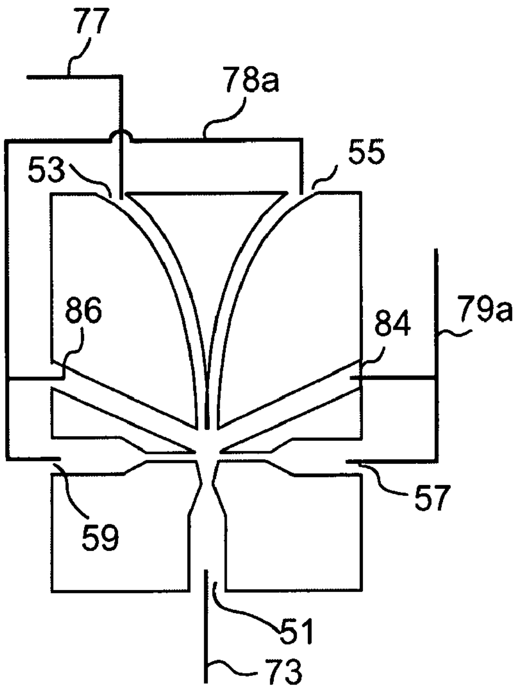
Figure 6:
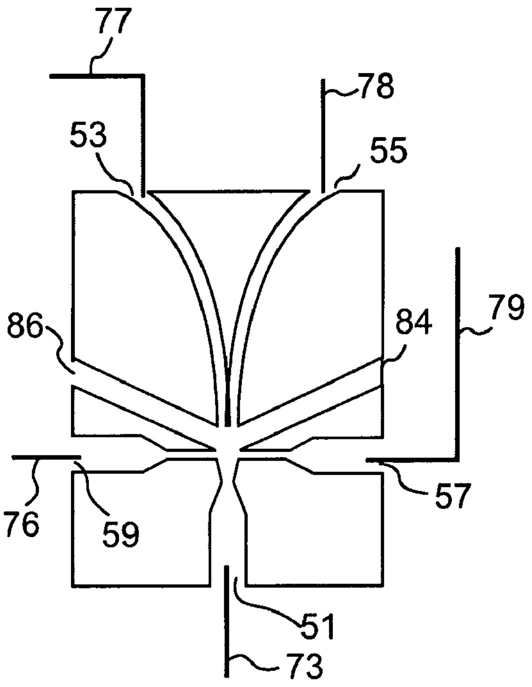
Figure 7:
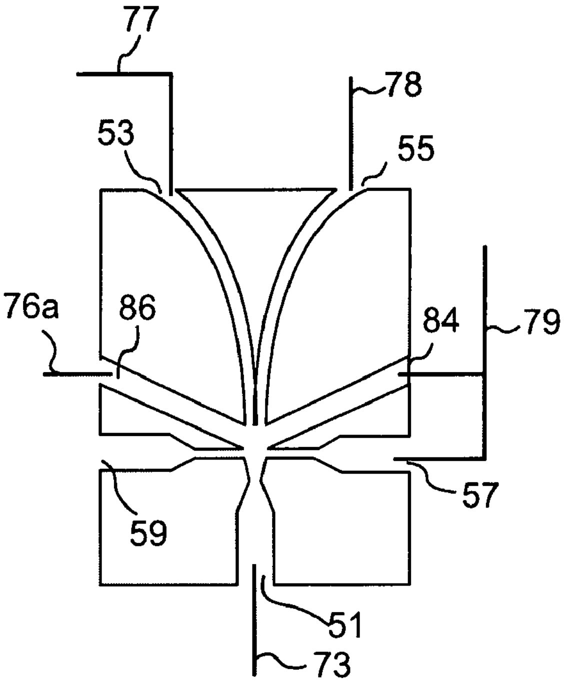

With reference to FIGS. 4-7, various exemplary flow connections for the fluidic amplifier 54 of FIG. 3 are described. In one exemplary embodiment, as shown in FIG. 4, a signal flow path 79*a* is connected to both the control port 57 and the valved port 84. The ambient port 55 and the input flow ports 59, 86 each communicate to atmosphere. Alternatively or additionally, the ambient port 55 and at least one of the input flow ports 59, 86 may communicate with each other via a flow path 78*a*, as shown in FIG. 5. In these exemplary configurations shown in FIGS. 4 and 5, both ports 57, 84 may be used for switching between the non-nebulizing and nebulizing modes. According to another exemplary embodiment, the fluidic amplifier 54 may only use either the control port 57 and/or the valved port 84, as shown in FIGS. 6 and 7, respectively.

Figure 8:
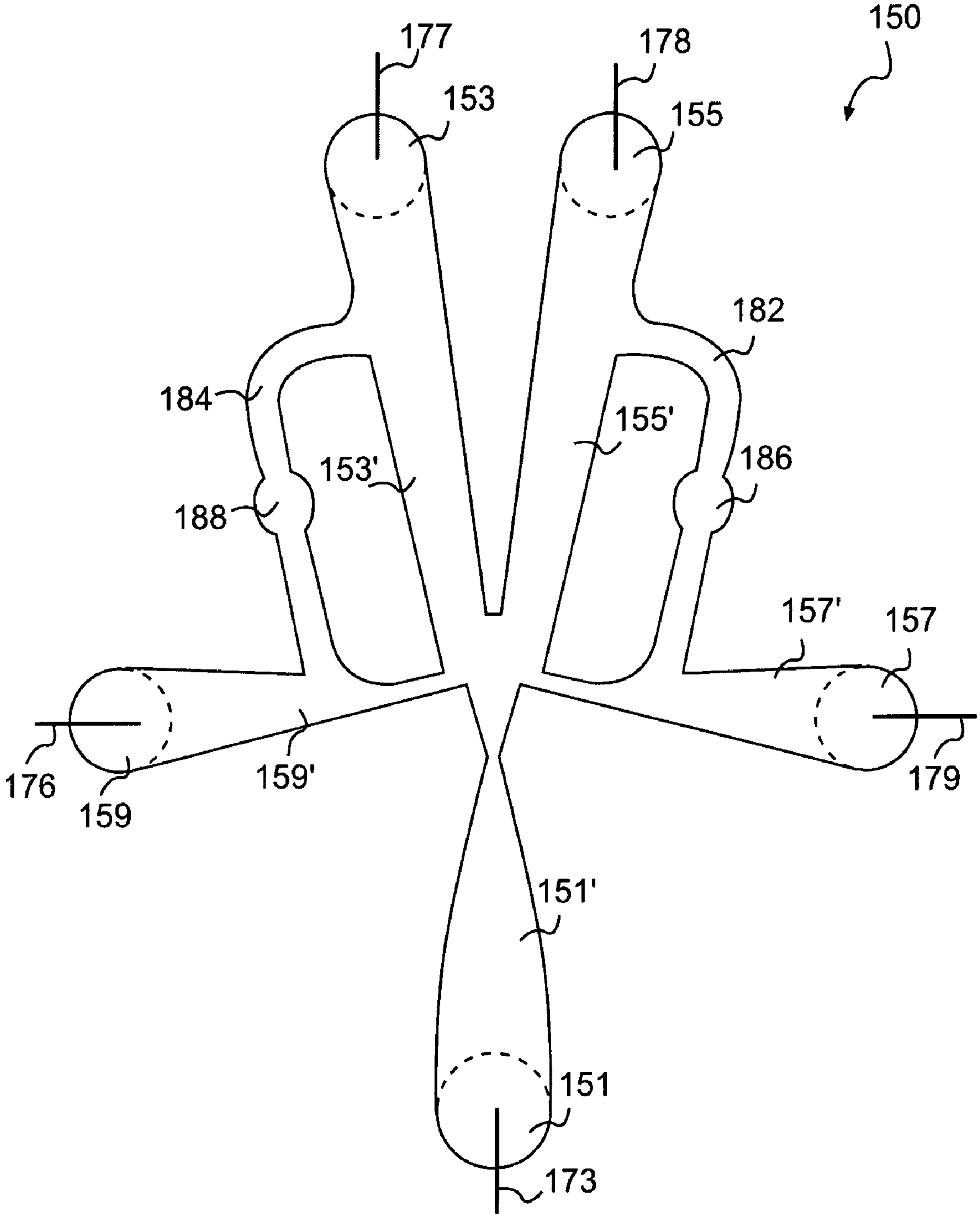
FIG. 8 is a schematic view of a fluidic amplifier, according to another exemplary embodiment of the invention.

FIG. 8 shows a schematic view of a fluidic amplifier 150, according to another exemplary embodiment consistent with the present invention. Fluidic amplifiers like that shown in FIG. 8 were designed by Bowles Fluidics Corporation of Columbia, Md., and have Identification Nos. M19912-011V14 and M20140-020V1. The fluidic amplifier 150 may be used in place of the fluidic amplifier 54 shown in the nebulizer system of FIGS. 1 and 2.

Similar to the fluidic amplifier 54 discussed above, the fluidic amplifier 150 of FIG. 8 may include an inlet port 151, a nebulizer port 153, an ambient port 155, a control port 157, and an input flow port 159. During the non-nebulizing mode, an input channel 151' leading from the input port 151 may be aligned with a nebulizer channel 153' leading to the nebulizer port 153, so that the control flow, when under no influence of pressure, may enter the fluidic amplifier 150 via the inlet port 151, pass through the input channel 151' and the nebulizer channel 153', and exit the fluidic amplifier 150 via the nebulizer port 153. During the nebulizing mode, a negative pressure at the control port 157 may cause the fluidic amplifier 150 to pull and redirect the control flow to the ambient port 155 via an ambient channel 155'. The flow connections 173, 176, 177, 178, 179 from the fluidic amplifier 150 to the rest of the nebulizer system are substantially identical to the embodiment shown in FIGS. 1 and 2 and, therefore, a detailed description relating to the flow connections is omitted here.

The fluidic amplifier 150 of FIG. 8 operates like those exemplary embodiments described above. A difference from the above-described embodiments is that this amplifier 150 comprises feedback conduits 182, 184 between a control channel 157' leading to the control port 157 and the ambient channel 155' and between an input flow channel 159' leading to the input flow port 159 and the nebulizer channel 153', respectively. In some exemplary embodiments, these conduits 182, 184 may include pocket regions 186, 188, as shown in FIG. 8. The feedback conduits 182, 184 may provide additional circulation paths to assist in flipping the control flow direction during patient inhalation, between the non-nebulizing and nebulizing modes.

Figure 9:
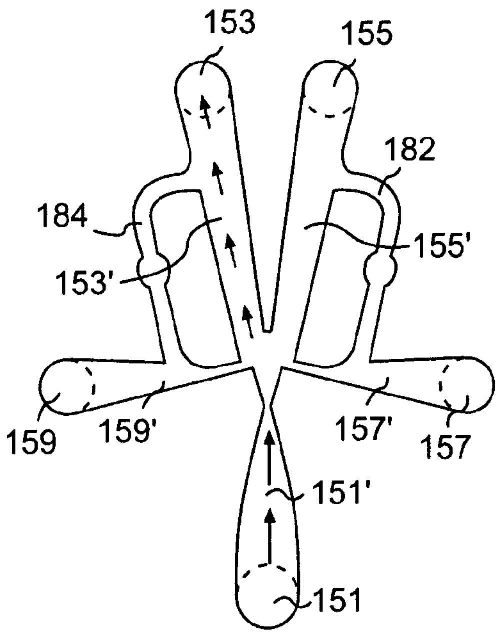
FIGS. 9-12 are schematic illustrations of a flow control process for the fluidic amplifier of FIG. 8, according to an exemplary embodiments of the invention.
Figure 10:
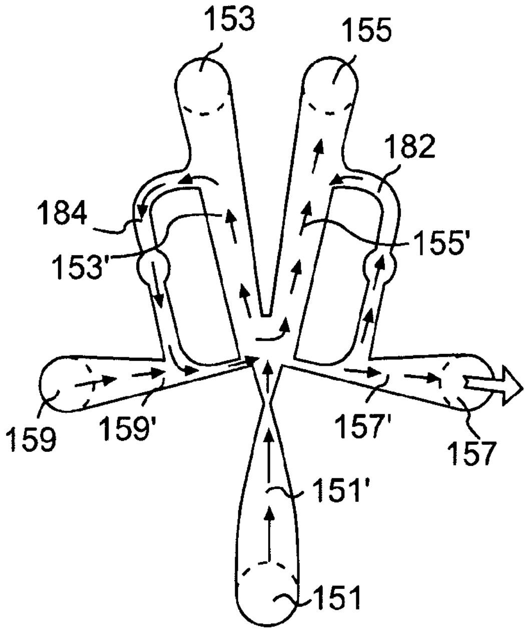

For example, FIGS. 9-12 illustrate flow directions of the control flow inside the fluidic amplifier 150 before (FIG. 9), during (FIGS. 10 and 11), and after (FIG. 12) patient inhalation. When the patient is not inhaling, as shown in FIG. 9, the control flow may enter the fluidic amplifier 150 via the inlet port 151, pass through the input channel 151' and the nebulizer channel 153', and exit via the nebulizer port 153. Upon start of patient inhalation, as shown in FIG. 10, the negative pressure created at the control port 157 may cause the control flow to immediately switch its direction from the nebulizer port 153 to the ambient port 155. The redirected control flow, together with the negative pressure at the control port 157 and the gas entering the inlet flow port 159, may cause the control flow that has already progressed into the nebulizer channel 153' to be circulated through the feedback conduit 184 and redirected to the ambient channel 155'. Redirecting the control flow existing in the nebulizer channel 153' immediately upon the patient inhalation may result in a faster interruption of the control flow to the conduit 26 and thereby a faster switching from the non-nebulizing mode to the nebulizing mode. Moreover, the feedback conduit 182 between the control channel 157' and the ambient channel 155' may cause a portion of the control flow entering into the control channel 157' to be redirected to the ambient channel 155'.

Figure 11:
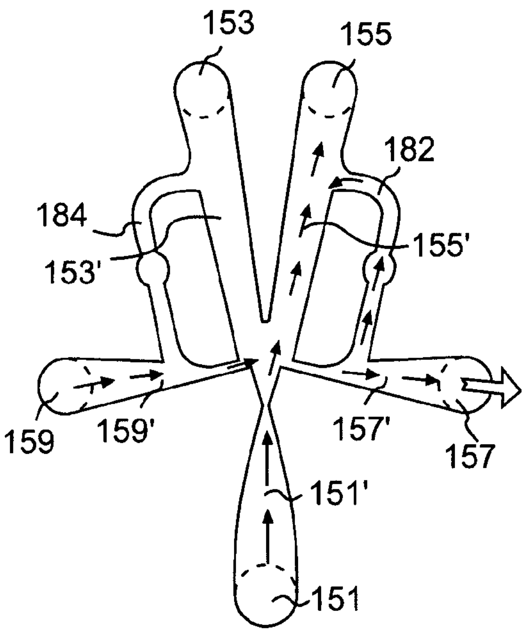
Figure 12:
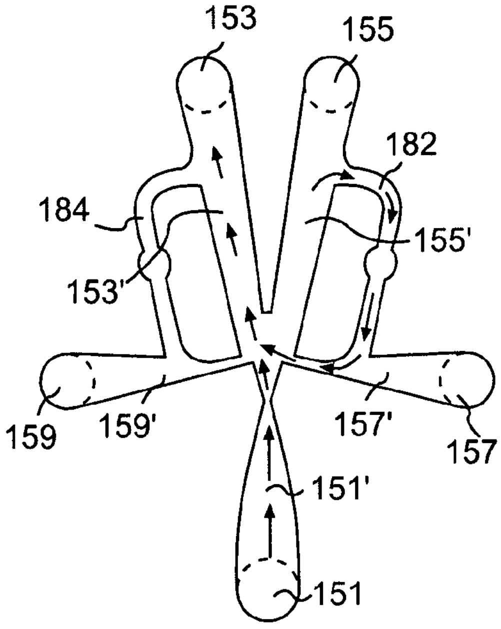

Once the control flow is completely switched to the nebulizing mode, as shown in FIG. 11, the control flow from the inlet port 151 may be directed to the ambient port 155 via the ambient channel 155'. At this stage, the feedback conduit 182 may continue to redirect a portion of the control flow entered into the control channel 157 to the ambient channel 155'. When the patient inhalation stops, as shown in FIG. 12, the control flow direction may be immediately switched from the ambient port 155 to the nebulizer port 153. Similar to the switch from the nebulizer port 153 to the ambient port 155 at the start of patient inhalation, the control flow redirected to the nebulizer port 153 may cause the control flow that has already progressed into the ambient channel 155' to be circulated through the feedback conduit 182 and redirected to the nebulizer channel 153'. Again, redirecting the control flow existing in the ambient channel 155' immediately after the patient inhalation stops may result in a faster initiation of the control flow to the conduit 26 and thereby a faster switching from the nebulizing mode to the non-nebulizing mode.

Figure 14:
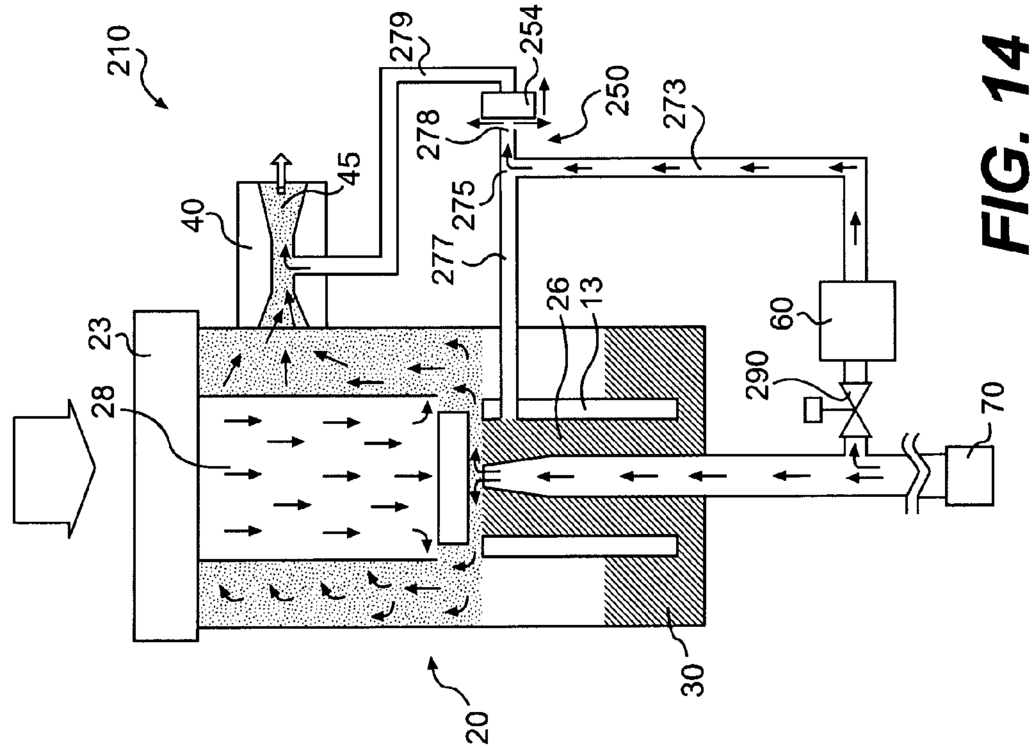
FIG. 14 is a schematic view of the nebulizer system of FIG. 13, illustrating a nebulizing mode.
Figure 13:
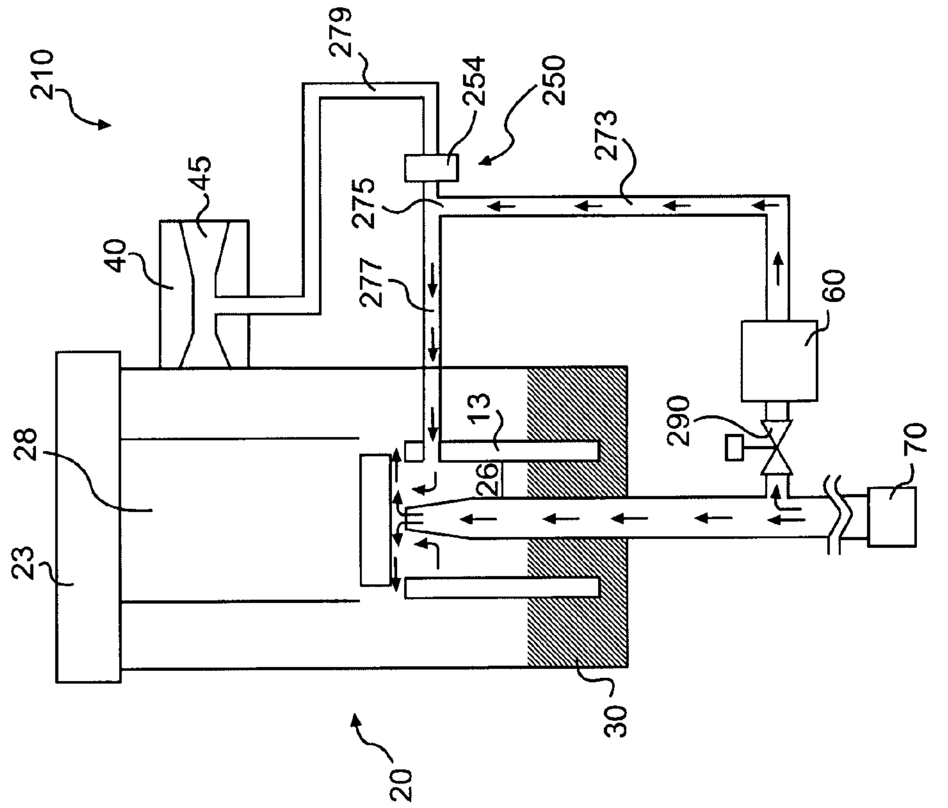
FIG. 13 is a schematic view of a nebulizer system, according to another exemplary embodiment of the invention, illustrating a non-nebulizing mode.

FIGS. 13 and 14 show schematic views of another exemplary embodiment of a breath-actuated nebulizer system 210, employing an alternative flow control system 250. The flow control system 250 may comprise a T-fitting 275 or similar mechanism to direct the control flow from the pressurized gas source 70 either to the conduit 26 inside the fluid sleeve 13 to stop nebulization or to atmosphere to initiate nebulization. For example, an opening 278 may be formed at one branch of the T-fitting 275, connected to the venturi 45 of the outlet member 40, to communicate with atmosphere. A movable valve 254 (e.g., a flexible diaphragm valve) or any other suitable relief valve may be placed over the opening 278. In a non-nebulizing mode, the valve 254 may remain in place to close the opening 278 and, therefore, the control flow may be directed by the T-fitting 275 to the conduit 26 inside the fluid sleeve 13, as shown in FIG. 13, to interrupt the entrainment of the medication thereto. In a nebulizing mode, the negative pressure generated by the patient inhalation may cause the valve 254 to lift from or otherwise open the opening 278, redirecting the control flow to atmosphere, as shown in FIG. 14. Redirecting the control flow to atmosphere may cause interruption of the control flow to the conduit 26 inside the fluid sleeve 13, permitting the medication 30 to enter the conduit 26 for nebulization.

While the fluid control system 50, including the fluid amplifiers 54, 150, has been described as being a separate component external to the nebulizer body 20, it should be understood that such a system 50 may be positioned within the nebulizer body 20. Moreover, all or a part of the control system 50 may be manufactured as a single-piece unit with the nebulizer body 20 (e.g., via injection molding). In addition, although various flow channels and flow paths have been depicted in the figures as being simplified flow connections, it should be understood that some of the flow channels and flow paths may have any geometrical shapes and configurations.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nebulizer comprising:

a body comprising a reservoir for holding medication;

a nozzle for emitting a jet of pressurized gas;

a fluid conduit in communication with the reservoir for delivery of the medication proximate the jet to produce an aerosol of medication;

a nebulizer outlet in communication with the body for delivery of the aerosol to a patient;

a control conduit in fluid communication with the fluid conduit for delivery of a control gas to the fluid conduit to prevent the delivery of the medication proximate the jet; and a fluidic amplifier configured to control the delivery of the control gas to the control conduit.

2. The nebulizer of claim 1, wherein the fluidic amplifier is configured to control the delivery of the control gas to the control conduit based on inhalation by the patient.

3. The nebulizer of claim 2, further comprising a signal conduit in fluid communication with the fluidic amplifier, the signal conduit for providing a negative pressure in response to the inhalation by the patient, the negative pressure for causing interruption of the delivery of the control gas to the fluid conduit via the control conduit.

4. The nebulizer of claim 2, wherein the fluidic amplifier comprises:

an inlet port for receiving the control gas;

a first outlet port;

a second outlet port for directing the control gas to the fluid conduit; and a control port configured to selectively switch a flow direction of the control gas between the first outlet port and the second outlet port based on the inhalation by the patient.

5. The nebulizer of claim 4, wherein the control port is in fluid communication with the nebulizer outlet.

6. The nebulizer of claim 4, wherein the fluidic amplifier is configured such that the inhalation causes a negative pressure in the control port, causing a flow direction of the control gas to switch from the second outlet port to the first outlet port.

7. The nebulizer of claim 4, wherein the first outlet port is in fluid communication with atmosphere or an interior of the body.

8. The nebulizer of claim 4, wherein the fluidic amplifier further comprises an input flow port disposed substantially opposite to the control port with respect to the inlet port.

9. The nebulizer of claim 8, wherein the first outlet port is in fluid communication with the input flow port.

10. The nebulizer of claim 4, wherein the control port comprises a valve configured to close in response to the inhalation by the patient.

11. The nebulizer of claim 1, wherein the pressurized gas and the control gas are delivered from a same source of gas, the control gas being branched off from the pressurized gas.

12. The nebulizer of claim 1, further comprising a flow regulator for controlling a flow of the control gas.

13. The nebulizer of claim 12, whether the flow regulator comprises a through-hole in a sleeve that at least partially defines the fluid conduit.

14. The nebulizer of claim 1, further comprising a stationary diverter to which the jet of pressurized gas is directed.

15. The nebulizer of claim 1, further comprising a venturi through which fluid passes when the patient inhales through the nebulizer outlet.

16. The nebulizer of claim 15, wherein the venturi is located inside the nebulizer outlet and is in fluid communication with the fluidic amplifier.

17. The nebulizer of claim 15, wherein the venturi is located inside the body and is in fluid communication with the fluidic amplifier.

18. The nebulizer of claim 1, further comprising an override mechanism configured to selectively disable operation of the fluid amplifier.

19. A nebulizer comprising:

a body comprising a reservoir for holding medication;

a nozzle for emitting a jet of pressurized gas;

a fluid conduit in communication with the reservoir for delivery of the medication proximate the jet to produce an aerosol of medication;

a nebulizer outlet in communication with the body for delivery of the aerosol to a patient;

a control conduit in fluid communication with the fluid conduit for delivery of a control gas to the fluid conduit to prevent the delivery of the medication proximate the jet; and a flow switch configured to control the delivery of the control gas to the control conduit based on inhalation by the patient, wherein the flow switch includes no part that moves in response to the inhalation by the patient.

20. The nebulizer of claim 19, further comprising a signal conduit in fluid communication with the flow switch, the signal conduit for providing a negative pressure in response to the inhalation by the patient, the negative pressure for causing interruption of the delivery of the control gas to the fluid conduit via the control conduit.

21. The nebulizer of claim 19, wherein the flow switch comprises:

an inlet port for receiving the control gas;

a first outlet port;

a second outlet port for directing the control gas to the fluid conduit; and a control port configured to selectively switch a flow direction of the control gas between the first outlet port and the second outlet port based on the inhalation by the patient.

22. The nebulizer of claim 21, wherein the control port is in fluid communication with the nebulizer outlet.

23. The nebulizer of claim 21, wherein the flow switch is configured such that the inhalation by the patient causes a negative pressure in the control port, causing a flow direction of the control gas to switch from the second outlet port to the first outlet port.

24. The nebulizer of claim 21, wherein the first outlet port is in fluid communication with atmosphere or an interior of the body.

25. The nebulizer of claim 21, wherein the flow switch further comprises an input flow port disposed substantially opposite to the control port with respect to the inlet port.

26. The nebulizer of claim 19, wherein the pressurized gas and the control gas are delivered from a same source of gas, the control gas being branched off from the pressurized gas.

27. The nebulizer of claim 19, further comprising a flow regulator for controlling a flow of the control gas.

28. The nebulizer of claim 27, wherein the flow regulator comprises a through-hole in a fluid sleeve that at least partially defines the fluid conduit.

29. The nebulizer of claim 19, further comprising a venturi through which fluid passes when the patient inhales through the nebulizer outlet.

30. The nebulizer of claim 29, wherein the venturi is located inside the nebulizer outlet and is in fluid communication with the flow switch.

31. The nebulizer of claim 29, wherein the venturi is located inside the body and is in fluid communication with the flow switch.

32. The nebulizer of claim 19, further comprising an override mechanism configured to selectively disable operation of the flow switch.

33. A nebulizer comprising:
a body comprising a reservoir for holding medication;
a nozzle for emitting a jet of pressurized gas;
a fluid conduit in communication with the reservoir for delivery of the medication proximate the jet to produce an aerosol of medication;
a nebulizer outlet in communication with the body for delivery of the aerosol to a patient;
a control conduit in fluid communication with the fluid conduit for delivery of a control gas to the fluid conduit to prevent the delivery of the medication proximate the jet; and
a flow switch comprising:
an inlet port for receiving the control gas;
a first outlet port;
a second outlet port for directing the control gas to the fluid conduit; and
a control member configured to selectively switch a flow direction of the control gas between the first outlet port and the second outlet port.

34. The nebulizer of claim 33, wherein the control member is configured to switch the flow direction based on inhalation by the patient.

35. The nebulizer of claim 34, wherein the control member comprises a control port in fluid communication with the nebulizer outlet via a signal conduit, the signal conduit providing a negative pressure in response to the inhalation by the patient for causing a flow direction of the control gas to switch from the second outlet port to the first outlet port, so as to interrupt the delivery of the control gas to the control conduit.

36. The nebulizer of claim 34, wherein the control member comprises a valve configured to selectively open the first outlet port in response to the inhalation by the patient, opening the first outlet port causing the flow direction of the control gas to switch from the second outlet port to the first outlet port.

37. The nebulizer of claim 33, wherein the flow switch comprises a T-junction with each branch constituting the inlet port, the first outlet port, and the second outlet port, respectively.

38. The nebulizer of claim 33, wherein the flow switch includes no part that moves in response to inhalation by the patient.

39. The nebulizer of claim 33, wherein the pressurized gas and the control gas are delivered from a same source of gas, the control gas being branched off from the pressurized gas.

40. The nebulizer of claim 33, further comprising a flow regulator for controlling a flow of the control gas.

41. The nebulizer of claim 40, wherein the flow regulator comprises a through-hole in a fluid sleeve that at least partially defines the fluid conduit.

42. The nebulizer of claim 33, further comprising a venturi through which fluid passes when the patient inhales through the nebulizer outlet.

43. The nebulizer of claim 33, further comprising an override mechanism configured to selectively disable operation of the flow switch.

44. A nebulizer comprising:
a body comprising a reservoir for holding medication;
a nozzle for emitting a jet of pressurized gas, the pressurized gas supplied to the nozzle via a main gas conduit;
a fluid conduit in communication with the reservoir for delivery of the medication proximate the jet to produce an aerosol of medication;
a nebulizer outlet in communication with an interior of the body for delivery of the aerosol to a patient;
a control conduit branching off from the main gas conduit and in fluid communication with the fluid conduit, the control conduit for delivery of a control gas to the fluid conduit to prevent the delivery of the medication proximate the jet; and
a control system configured to control the delivery of control gas to the control conduit.

45. The nebulizer of claim 44, wherein the control system is configured to control the delivery of control gas to the control conduit based on inhalation by the patient.

46. The nebulizer of claim 45, further comprising a signal conduit in fluid communication with the control system, the signal conduit for providing a negative pressure in response to the inhalation by the patient, the negative pressure for causing interruption of the delivery of the control gas to the fluid conduit via the control conduit.

47. The nebulizer of claim 45, wherein the control system comprises:
an inlet port for receiving the control gas;
a first outlet port;
a second outlet port for directing the control gas to the fluid conduit; and
a control port configured to selectively switch a flow direction of the control gas between the first outlet port and the second outlet port based on the inhalation by the patient.

48. The nebulizer of claim 44, further comprising a flow regulator for controlling a flow of the control gas.

49. The nebulizer of claim 48, wherein the flow regulator comprises a through-hole in a fluid sleeve that at least partially defines the fluid conduit.

50. The nebulizer of claim 44, further comprising a stationary diverter to which the jet of pressurized gas is directed.

51. The nebulizer of claim 44, wherein the control system includes no part that moves in response to the inhalation by the patient.

52. The nebulizer of claim 44, further comprising a venturi through which fluid passes when patient inhales through the nebulizer outlet.

53. The nebulizer of claim 44, further comprising an override mechanism configured to selectively disable operation of the control system.

54. A method of controlling a nebulization process, comprising:
providing medication in a reservoir within a body, the body comprising an outlet for inhalation by a patient;
emitting a jet of pressurized gas into the body;
providing a fluid conduit in communication with the reservoir for delivery of the medication proximate the jet;
preventing delivery of the medication proximate the jet by delivering a control gas to the fluid conduit via a control conduit; and
using a fluidic amplifier to interrupt the delivery of the control gas to the control conduit based on inhalation by the patient, the interruption permitting delivery of the medication proximate the jet to produce an aerosol of medication.

55. The method of claim 54, wherein the fluidic amplifier comprises:
an inlet port for receiving the control gas;
a first outlet port;

a second outlet port for directing the control gas to the fluid conduit; and a control port configured to selectively switch a flow direction of the control gas between the first outlet port and the second outlet port based on the inhalation by the patient.

56. The method of claim 55, wherein the control port is in fluid communication with the outlet.

57. The method of claim 56, further comprising creating a negative pressure in the control port by inhalation of the patient, the negative pressure causing a flow direction of the control gas to switch from the second outlet port to the first outlet port.

58. The method of claim 55, further comprising biasing the control gas to flow from the inlet port to the second outlet port when the patient is not inhaling.

59. The method of claim 54, wherein the pressurized gas and the control gas are delivered from a same source of gas, the control gas being branched off from the pressurized gas.

60. The method of claim 54, further comprising regulating a flow of the control gas to the control conduit via a flow regulator.

61. The method of claim 54, further comprising directing the jet of pressurized gas towards a stationary diverter.

62. The method of claim 54, wherein the fluidic amplifier includes no part that moves in response to the inhalation by the patient.

63. A method of controlling a nebulization process, comprising:

providing medication in a reservoir within a body, the body comprising an outlet for inhalation by a patient;

emitting a jet of pressurized gas;

providing a fluid conduit in communication with the reservoir for delivery of the medication proximate the jet;

preventing delivery of the medication proximate the jet by delivering a control gas to the fluid conduit; and using a flow switch to interrupt the delivery of the control gas to the control conduit based on inhalation by the patient, the interruption permitting delivery of the medication proximate the jet to produce an aerosol of medication, wherein the flow switch includes no part that moves in response to the inhalation by the patient.

64. The method of claim 63, wherein the flow switch comprises:

an inlet port for receiving the control gas;

a first outlet port;

a second outlet port for directing the control gas to the fluid conduit; and a control port configured to selectively switch a flow direction of the control gas between the first outlet port and the second outlet port based on the inhalation by the patient.

65. The method of claim 64, wherein the control port is in fluid communication with the outlet.

66. The method of claim 65, further comprising creating a negative pressure in the control port by inhalation of the patient, the negative pressure causing a flow direction of the control gas to switch from the second outlet port to the first outlet port.

67. The method of claim 64, further comprising biasing the control gas to flow from the inlet port to the second outlet port when the patient is not inhaling.

68. The method of claim 63, wherein the pressurized gas and the control gas are delivered from a same source of gas, the control gas being branched off from the pressurized gas.

69. A method of controlling a nebulization process, comprising:

providing medication in a reservoir within a body, the body comprising an outlet for inhalation by a patient;

emitting a jet of pressurized gas;

providing a fluid conduit in communication with the reservoir for delivery of the medication proximate the jet;

preventing delivery of the medication proximate the jet by delivering a control gas to the fluid conduit via a control conduit; and using a flow switch to interrupt the delivery of the control gas to the control conduit, the flow switch comprising:

an inlet port for receiving the control gas;

a first outlet port;

a second outlet port for directing the control gas to the fluid conduit; and a control member configured to switch a flow direction of the control gas between the first outlet port and the second outlet port.

70. The method of claim 69, wherein the control member is configured to switch the flow direction of the control gas between the first outlet port and the second outlet port based on inhalation by the patient.

71. The method of claim 69, wherein the control member comprises a control port in fluid communication with the outlet via a signal conduit, the signal conduit providing a negative pressure in response to the inhalation by the patient for causing a flow direction of the control gas to switch from the second outlet port to the first outlet port, so as to interrupt the delivery of the control gas to the control conduit.

72. The method of claim 69, wherein the control member comprises a valve configured to selectively open the first outlet port in response to the inhalation by the patient, opening the first outlet port causing the flow direction of the control gas to switch from the second outlet port to the first outlet port.

73. The method of claim 69, wherein the flow switch comprises a T-junction with each branch constituting the inlet port, the first outlet port, and the second outlet port, respectively.

74. The method of claim 69, wherein the pressurized gas and the control gas are delivered from a same source of gas, the control gas being branched off from the pressurized gas.

75. A method of controlling a nebulization process, comprising:

providing medication in a reservoir within a body, the body comprising an outlet for inhalation by a patient;

emitting a jet of pressurized gas, the pressurized gas supplied via a main gas conduit;

providing a fluid conduit in communication with the reservoir for delivery of the medication proximate the jet;

preventing delivery of the medication proximate the jet by delivering a control gas to the fluid conduit via a control conduit; and using a control system to interrupt the delivery of the control gas to the control conduit based on inhalation by the patient, wherein the control conduit branches off from the main gas conduit and is in fluid communication with the fluid conduit.

76. The method of claim 75, wherein the control system comprises:

an inlet port for receiving the control gas;

a first outlet port;

a second outlet port for directing the control gas to the fluid conduit; and a control port configured to selectively switch a flow direction of the control gas between the first outlet port and the second outlet port based on the inhalation by the patient.

77. The method of claim 76, further comprising connecting the control port to the outlet, so that the inhalation by the patient creates a negative pressure for causing the flow direction of the control gas to switch from the second outlet port to the first outlet port, so as to interrupt the delivery of the control gas to the control conduit.

78. The method of claim 75, wherein the control system includes no part that moves in response to the inhalation by the patient.

* * * * *

UNITED STATES PATENT AND TRADEMARK OFFICE

CERTIFICATE OF CORRECTION

PATENT NO. : 7,841,336 B2
APPLICATION NO. : 11/729720
DATED : November 30, 2010
INVENTOR(S) : Steven M. Harrington et al.

It is certified that error appears in the above-identified patent and that said Letters Patent is hereby corrected as shown below:

First Page, Column 1 (Title), line 1, delete “NEBULIZE” and insert in place thereof --NEBULIZER--.

Column 1, line 1, delete “NEBULIZE” and insert in place thereof --NEBULIZER--.

Signed and Sealed this
Twenty-second Day of February, 2011

David J. Kappos
*Director of the United States Patent and Trademark Office*